United States Patent [19]

Marko et al.

[11] Patent Number: 4,578,494

[45] Date of Patent: Mar. 25, 1986

[54] PREPARATION OF POLYSILOXANES FROM HALOSILANES

[75] Inventors: Ollie W. Marko; Robert D. Steinmeyer, both of Carrollton, Ky.; Stefan Rentsch, Midland, Mich.

[73] Assignee: Dow Corning Corporation, Midland, Mich.

[21] Appl. No.: 744,708

[22] Filed: Jun. 14, 1985

[51] Int. Cl.$^4$ .............................. C07F 7/08; C07F 7/18
[52] U.S. Cl. ................................... 556/452; 556/460; 556/461; 528/14; 528/15; 528/16; 528/17; 528/18
[58] Field of Search ............... 556/452, 460, 461

[56] References Cited

U.S. PATENT DOCUMENTS

| | | | |
|---|---|---|---|
| 3,021,297 | 2/1962 | George | 556/460 X |
| 3,235,579 | 2/1966 | Brown et al. | 556/452 X |
| 3,398,173 | 8/1968 | Goosens | 556/460 X |
| 3,687,642 | 8/1972 | Koerner et al. | 556/460 X |
| 4,073,801 | 2/1978 | Moretto et al. | 556/452 X |
| 4,161,487 | 7/1979 | Börner et al. | 556/452 |
| 4,276,425 | 6/1981 | Burkhardt et al. | 556/460 |
| 4,382,145 | 5/1983 | Yeboah | 556/452 X |

*Primary Examiner*—Paul F. Shaver
*Attorney, Agent, or Firm*—Robert L. McKellar

[57] ABSTRACT

This invention relates to a process for the preparation of polysiloxanes by reacting halosilanes in the presence of metal oxides and sulfolane. Preferred metal oxides include antimony (III) oxide, antimony (V) oxide, cadmium oxide, calcium oxide, copper (II) oxide, indium oxide, iron (II) oxide, iron (III) oxide, magnesium oxide, manganese (II) oxide, mercury (II) oxide, nickel (II) oxide, thallium (III) oxide, tin (II) oxide, and zinc oxide. Improved yields and rates of reaction can be observed with the process of this invention.

30 Claims, No Drawings

PREPARATION OF POLYSILOXANES FROM HALOSILANES

BACKGROUND OF THE INVENTION

This invention relates to a process for the preparation of polysiloxanes from halosilanes. More specifically, this invention relates to a process for the preparation of polysiloxanes by reacting halosilanes in the presence of metal oxides and sulfolane.

Polysiloxanes are most commonly prepared by the hydrolysis of halosilanes. One alternative method of preparing polysiloxanes involves the reaction of halosilanes in the presence of metal oxides. Vyle and Kipping in *J. Chem. Soc.*, 2616 (1924) reported that a viscous oil was obtained when diphenyldichlorosilane was reacted with mercuric oxide in a toluene solution. The viscous oil was presumably a polysiloxanes.

Takiguchi et al. in *J. Org. Chem.*, 25, 310(1969) prepared hexaphenylcyclotrisiloxane by the reaction of diphenyldichlorosilane with zinc oxide. Other anhydrous metal oxides, including cupric oxide, lead oxide, silver oxide and manganese dioxide, were found to react in a similar manner.

Frainnet et al. in *Bull. Soc. Chim. France*, 1480(1960) found that polysiloxanes could be prepared by reacting dimethyldichlorosilane and methylhydrogendichlorosilane with iron (III) oxide.

Andrianov et al. in *Zhural Obshchei Khimii*, 32, 3951 (1962) reported that dimethyldichlorosilane and iron (III) oxide only react in the presence of a small amount of water or hydrogen chloride.

Shaw et al. in U.S. Pat. No. 2,580,852 (issued Jan. 1, 1952) reported the preparation of polysiloxanes by refluxing a dialkyldichlorosilane with cupric oxide under anhydrous conditions.

Hyde in U.S. Pat. No. 2,571,884 (issued Oct. 16, 1951) prepared linear chlorine endblocked siloxanes by reaction of silicon tetrachloride with a metallic oxide selected from the group $MnO_2$, CuO, $Cu_2O$, CaO, ZnO, MgO, $Fe_2O_3$, $Ag_2O$, and HgO in the presence of a solvent which contained either nitro groups or nitrile groups.

Hyde in U.S. Pat. No. 2,629,726 (issued Feb. 24, 1953) prepared polysiloxanes by reacting halosilanes with lead oxide, magnesium oxide, calcium oxide, copper oxide, or zinc oxide in the presence of a solvent which contained either nitro groups or nitrile groups.

Pike in U.S. Pat. No. 3,110,720 (issued Nov. 12, 1963) formed cyclic polysiloxanes by reacting dialkyldichlorosilanes with calcium oxide, sodium oxide, potasium oxide, or lithium oxide at a temperature of at least 200° C. in the absence of water or any organic solvent.

It is one object of this present invention to provide a new method for the preparation of polysiloxanes from halosilanes. It is another object to provide a method for the production of polysiloxanes from halosilanes in the absence of water. It is still another object to provide a more efficient process for the production of polysiloxanes from halosilanes in the absence of water. Still other objects will be apparent from a consideration of this specification.

THE INVENTION

This invention relates to a method for producing polysiloxanes, said method comprising (1) reacting a halosilane or mixture of halosilanes in the presence of a metal oxide or mixture of metal oxides and sulfolane wherein polysiloxanes are formed from said halosilane or mixture of halosilanes and wherein said metal oxide or mixture of metal oxides forms a metal halogen complex or mixed metal halogen complex with said sulfolane and (2) thereafter separating the polysiloxanes.

This invention also relates to a method for producing polysiloxanes, said method comprising (1) reacting under essentially anhydrous conditions a halosilane or mixture of halosilanes in the presence of a metal oxide or mixture of metal oxides and sulfolane wherein polysiloxanes are formed from said halosilane or mixture of halosilanes and wherein said metal oxide or mixture of metal oxides forms a metal halogen complex or mixed metal halogen complex with said sulfolane and (2) thereafter separating the polysiloxanes.

This invention further relates to a method for producing polysiloxanes, said method comprising (1) reacting a halosilane or mixture of halosilanes in the presence of a metal oxide or mixture of metal oxides and sulfolane wherein said metal oxide or mixture of metal oxides are selected from the group consisting of antimony (III) oxide, antimony (V) oxide, cadmium oxide, calcium oxide, copper (II) oxide, indium oxide, iron (II) oxide, iron (III) oxide, mercury (II) oxide, magnesium oxide, manganese (II) oxide, nickel (II) oxide, thallium (III) oxide, tin (II) oxide, and zinc oxide and (2) thereafter separating the polysiloxanes.

This invention still further relates to a method for producing polysiloxanes, said method comprising (1) reacting under essentially anhydrous conditions a halosilane or mixture of halosilanes in the presence of a metal oxide or mixture of metal oxides and sulfolane wherein said metal oxide or mixture of metal oxides are selected from the group consisting of antimony (III) oxide, antimony (V) oxide, cadmium oxide, calcium oxide, copper (II) oxide, indium oxide, iron (II) oxide, iron (III) oxide, mercury (II) oxide, magnesium oxide, manganese (II) oxide, nickel (II) oxide, thallium (III) oxide, tin (II) oxide, and zinc oxide and (2) thereafter separating the polysiloxanes.

By "polysiloxanes" the inventors mean low molecular weight cyclics siloxanes, low molecular weight linear siloxanes, oligomeric siloxanes, as well as high molecular weight siloxane polymers.

Sulfolane is tetrahydrothiophene-1,1-dioxide and is available commercially in essentially anhydrous form. The sulfolane used in this invention can contain limited amounts, defined as less than 1000 ppm, water. It is preferred that the sulfolane used be essentially anhydrous. By "essentially anhydrous" we mean that the sulfolane contains less than 500 ppm water. The sulfolane may be dried using molecular sieves if desired.

The method of this invention is carried out by reacting a halosilane or mixture of halosilanes with a metal oxide and sulfolane or two or more metal oxides and sulfolane. Suitable halosilanes include fluorosilanes, bromosilanes, chlorosilanes, and iodosilanes. Bromosilanes and chlorosilanes are preferred for the practice of this invention. Chlorosilanes are most preferred for the practice of this invention. The halosilanes suitable for use in this invention include halosilanes which can be polymerized by water hyrolysis as well as halosilanes which contain substituents which react with either water or acid which cannot be polymerized by water hydrolysis. Suitable halosilanes can be described by the general formula $$R_ySiX_{(4-y)}$$

where R is an organic radical attached to silicon through a Si—C bond, or an organic radical attached to silicon through a Si—O bond, or hydrogen; where X is a halogen; and where y is 1 or 2. Examples of suitable R groups attached to silicon through a Si—C bond include alkyl radicals, aryl radicals, aryl hydrocarbon radicals, substituted alkyl radicals, substituted aryl radicals, and substituted aryl hydrocarbon radicals. Specific examples of such R groups attached to silicon through a Si—C bond include methyl, ethyl, propyl, butyl, cyclohexyl, phenyl, benzyl, vinyl, allyl, trifluoropropyl, and the like. Examples of suitable R groups attached to silicon through a Si—O bond include alkoxy radicals, aryloxy radicals, substituted alkoxy radicals, and substituted aryloxy radicals. Suitable alkoxy and aryloxy type radicals are of the general formula —OR' where R' is an alkyl, aryl, substituted alkyl, or substituted aryl radical. Specific examples of such R groups attached to silicon through a Si—O bond include methoxy, ethoxy, propoxy, butoxy, phenoxy, benzoxy, vinyloxy, and the like. The R group may also be a substituted alkyl, aryl, aryl hydrocarbon, alkoxy, or aryloxy radical as noted above. The substituents on such R radicals is not especially limited. Examples of such substituents include amines, carboxylic acids, hydroxyls, epoxys, aromatics, halides, ethers, aldehydes, ketones, and the like. The R groups may contain substituents which are reactive to water or acid. Indeed such reactive R groups-containing halosilanes are especially suitable for polymerization by the process of this invention because the polymerization can take place in the absence of water and acids. X in the above formula is a fluorine, bromine, chlorine, or iodine radical. Preferably X is chlorine or bromine. Most preferably X is chlorine. The value of y is either 1 or 2.

Specific examples of halosilanes suitable for use in this invention include trichlorosilane, dichlorosilane, methyldichlorosilane, dimethyldichlorosilane, dimethyldifluorosilane, dimethyldibromosilane, dimethyldiisodosilane, phenyldichlorosilane, diphenyldichlorosilane, methyltrichlorosilane, propyltrichlorosilane, octadecyldichlorosilane, trifluorotolyltrichlorosilane, bistrifluorotolyldichlorosilane, chlorophenylmethyldichlorosilane, xenyltrichlorosilane, bromoxenyltrichlorosilane, chloromethyltrichlorosilane, trifluoromethyldifluorobromosilane, allytrichlorosilane, bromoethynyltrichlorosilane, methyltriiodosilane, methylchlorodiiodosilane, trichlorovinyltrichlorosilane, 3-(dimethylamino)propyltribromosilane, methylmethoxydichlorosilane, methoxytrichlorosilane, methyl(tertbutoxy)dichlorosilane, methoxytribromosilane, chloromethoxytrichlorosilane, ethoxytrichlorosilane, ethoxydichlorosilane, dimethoxydichlorosilane, propoxytrichlorosilane, methoxyethoxydichlorosilane, and the like. Other suitable halosilanes, for example, may be found in Bazant et al. "Organosilicon Compounds", Volume 2, Part 1, Academic Press, New York (1965). These halosilanes are well known in the art and may be prepared by well established procedures.

Mixtures of halosilanes may be used in this invention to prepare polysiloxanes. For example, a mixture of dimethyldichlorosilane and methyltrichlorosilane may be reacted with a metal oxide/sulfolane mixture to prepare a polysiloxane containing $(CH_3)_2SiO$ and $CH_3SiO_{3/2}$ units. The reaction mixtures, in addition to containing $RSiX_3$ and/or $R_2SiX_2$ halosilanes, may also contain small amounts of $R_3SiX$ and $SiX_4$ silanes. A $R_3SiX$ silane, if present, will provide —$SiR_3$ endblocking groups. A $SiX_4$ silane, if present, will provide for extensive crosslinking. The $R_3SiX$ silane should be present at levels less than about 20 weight percent based on the total weight of the halosilane mixture; the $SiX_4$ silane should be present at levels less than about 10 weight precent and preferably at levels less than about 5 weight percent.

The halosilane or mixture of halosilanes are reacted with a metal oxide or mixture of metal oxides in the presence of sulfolane. The metal oxide or mixture of metal oxides are preferred to be essentially anhydrous. Although not wishing to be held to such a theory it is thought that the metal oxides employed in the practice of this invention must be capable of forming metal halogen complexes with sulfolane as a ligand in the presence of the halosilanes. It is further thought that the formation of such a metal halogen sufolane complex acts as a driving force in the polymerization reaction. Not all metal oxides which are capable of forming such metal halogen complexes will promote the polymerization of halosilanes. For example, tin (IV) oxide did not promote the polymerization of dimethyldichlorosilane in the presence of sulfolane. The reasons for this failure are not clear. Routine experimentation may be necessary to determine if a given metal oxide or mixture of metal oxides, which are capable of forming a metal halogen sulfolane complex, will promote the polymerization of a given halosilane or halosilanes to give polysiloxanes as required by this invention. Neither aluminia nor cobalt (III) oxide, which are not reported to form a metal halogen sulfolane complex, promoted the polymerization of chlorosilanes.

During the course of the reaction a metal halogen sulfolane complex is thought to be formed. The metal halogen sulfolane complex may either be a metal halogen adduct of sulfolane or a metal solvate of sulfolane. Metal halogen adducts of sulfolane have the general formula $$MX_n(\text{sulfolane})_m$$

where M is the metal ion of valance n, X is a halogen and m is at least one. Typically m will be between 1 and 6 depending on the valance and coordination number of the metal ion. Metal halogen solvates of sulfolane have the general formula $$M'(\text{sulfolane})_6(M''X_n)_2$$

where M' is a metal ion of valance of 2, M" is a metal ion of valance (n−2), and X is a halogen. The formation of such complexes is described in detail by J. Reedijk et al. in *Inorganica Chimica Acta*, 3:2, 271 (1969) which is hereby incorporated by reference.

Suitable metal oxides for use in this invention include antimony (III) oxide, antimony (V) oxide, cadmium oxide, calcium oxide, copper (II) oxide, indium oxide, iron (II) oxide, iron (III) oxide, magnesium oxide, manganese (II) oxide, mercury (II) oxide, nickel (II) oxide, thallium (III) oxide, tin (II) oxide, and zinc oxide. Other metal oxides may be used in this invention so long as they are capable of forming a metal halide sulfolane complex in the presence of halosilanes and they promote the polymerization of halosilanes in the presence of sulfolane to produce polysilanes.

Preferred metal oxides include antimony (III) oxide, antimony (V) oxide, cadmium oxide, calcium oxide, indium oxide, iron (II) oxide, iron (III) oxide, magnesium oxide, mercury (II) oxide, thallium (III) oxide, tin (II) oxide, and zinc oxide. More preferred metal oxides include cadmium oxide, calcium oxide, iron (II) oxide, iron (III) oxide, magnesium oxide, mercury (II) oxide, and tin (II) oxide. The most preferred metal oxide is iron (III) oxide. Mixtures of metal oxides may also be used in this invention. For example, a mixture of iron (II) and iron (III) oxides (i.e. $Fe_3O_4$ or rust) could be used in the practice of this invention.

The temperature of the reaction is not critical. Pure sulfolane freezes at about 26° C. The reaction temperature should be sufficiently high so that the sulfolane will not freeze and that the reaction will proceed at a satisfactory rate. The halosilanes and any added solvent will significantly lower the freezing point of sulfolane. It is preferred that the reaction temperature be at room temperature or above. Sulfolane is reported to thermally decompose at a low rate at temperatures of 180°-220° C. Above 220° C. decomposition becomes rapid with such excess temperatures causing the sulfolane "to crack" to a dark polymer and $SO_2$. Therefore it is preferred that the reaction temperature be kept below 180° C. Generally a reaction temperature of between room temperature and 100° C. is preferred. If organic solvents are employed in the reaction mixture it is preferred that the temperature be kept at or below the reflux temperature. The pressure at which the reaction is carried out is not critical. It is preferred that the pressure be at or close to atmospheric for ease of operation.

The amount of metal oxide and sulfolane present relative to the halosilane is not especially critical. The amounts of metal oxide and sulfolane present will effect the relative amounts of low molecular weight polysiloxanes and high molecular weight polysiloxanes produced as well as the reaction rate. It is preferred that the metal oxide is present in an amount sufficient to react will all of the halogen present in the form of Si—X bonds in the halosilanes. It is also preferred that the sulfolane is present in the amount sufficient to complex with essentially all of the metal from the metal oxide in the form of the metal halide sulfolane complex. In many cases an excess of sulfolane may be preferred. Higher or lower amounts of the metal oxide and sulfolane may be used. In some cases such lower or higher amounts may be preferred.

Organic solvents may be used in the process of this invention. Any organic solvent used should not react with either the halosilanes or the sulfolane. The organic solvent may act as a separation aid depending upon the relative solubilities of the polysiloxane, sulfolane, and metal halide sulfolane complex. Preferred solvents would be the linear alkanes which are essentially insoluble in sulfolane. By "essentially insoluble" we mean that the organic solvent is soluble in the sulfolane at less than about 0.5 weight percent. Hexane is an example of such a preferred organic solvent which functions as a separation aid. Other essentially insoluble organic solvents may be used.

After completion of the reaction to the desired degree the polysiloxanes are collected. The separation of the polysiloxanes from the reaction mixture can be carried out by conventional techniques and procedures. Physical techniques such as phase separation are especially useful since the polysiloxanes formed are essentially insoluble in sulfolane. An organic solvent in which the polysiloxane is soluble and the sulfolane is essentially insoluble can aid in this phase separation. The organic solvent can be present during the reaction, as noted above, or can be added after completion of the reaction. Other separation procedures can be used.

After separation of the polysiloxane from the reaction mixture the sulfolane may be recovered by treating any metal halide sulfolane complex formed with water or alcoholic potassium hydroxide. The recovered sulfolane may be reused in the process of this invention.

So that those skilled in the art can better appreciate and understand the invention, the following examples are given. The following procedure, unless otherwise indicated, was used in the examples. A masterbatch solution containing 1600 g hexane, 400 g dimethyldichlorosilane, and 100 g nonane was prepared. Nonane was used as an internal standard for gas liquid chromatography (GLC) analysis. To 100 g of the masterbatch solution, which contained 0.31 mole chloride ion, was added a stiochiometrically equivalent amount of oxygen from a metal oxide. The resulting mixture was refluxed two hours and then analyzed by GLC. After cooling the mixture to 30°-40° C., 233 g of sulfolane (six molar equivalents based on the starting chloride content) was added to the reaction mixture. The sulfolane was dried over molecular sieves prior to use and contained less than 400 ppm water. The mixture was stirred for one additional hour without heating. In the cases where sulfolane promoted the formation of chlorine endblocked low molecular weight linear polysiloxanes a mild exotherm was observed upon addition of the sulfolane. After the one hour stirring, the hexane layer containing the polysiloxanes was collected and analyzed by GLC and gel permeation chromatography (GPC).

GLC analysis was carried out with a Hewlett-Packard 5710 gas chromotograph equipped with a ⅛ inch by 6 foot 10 percent SE30 on Chromosorb W HP column and a thermal conductivity detector. All GLC results are reported in area percents. Nonane was used as the internal standard. In some cases the individual cyclic or linear percentages do not add up to the reported "total cyclic" or "total linear"; in such cases other cyclic or linear low molecular weight polysiloxanes other than the specific ones listed were found. The following shorthand nomenclature is used in the examples for the polysiloxanes found. "Cl" is used to represent the $Cl(CH_3)_2SiO_{178}$-endblocking group and "D" represent the $(CH_3)_2SiO$ group. For example chlorine endblocked linear siloxane

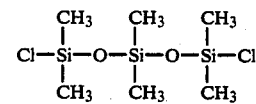

is represented in this shorthand system as "ClDCl". The cyclic hexamethylcyclotrisiloxane is represented by "D3".

High molecular weight polysiloxanes were analyzed by GPC. The GPC equipment was a Model HP1090 liquid chromatography manufactured by Hewlett Packard. GPC peak molecular weights were determined relative to polystyrene standards using toluene as the solvent. The reported molecular weights are estimated to be about 10-20 percent low.

EXAMPLE 1

The metal oxide used in this example was nickel oxide. NiO (23.3 g) was added to 100 g of the masterbatch solution described above. After refluxing for two hours the reaction mixture was analyzed by GLC. Sulfolane (223 g) was then added at 30°–40° C. and the reaction allowed to continue for one hour. The reaction mixture obtained after the sulfolane promoted reaction was also analyzed by GLC. The GLC results (in area percents) are presented in the following Table.

TABLE I

| | REACTANTS | |
|---|---|---|
| PRODUCTS | NiO | NiO + sulfolane |
| Cyclics: | | |
| D3 (%): | 0.03 | 0.08 |
| D4 (%): | 0.40 | 0.38 |
| D5 (%): | 0.17 | 0.14 |
| D6 (%): | 0.08 | 0.06 |
| TOTAL (%): | 0.68 | 0.96 |
| Linears: | | |
| ClDCl (%): | 1.18 | 1.32 |
| ClD2Cl (%): | 1.25 | 1.88 |
| ClD3Cl (%): | 0.68 | 0.94 |
| ClD4Cl (%): | 0.24 | 0.30 |
| TOTAL (%): | 3.35 | 4.44 |

The amount of dimethyldichlorosilane consumed in the reaction with the metal oxide alone was 10 area percent. The amount of dimethyldichlorosilane consumed in the reaction in the presence of the metal oxide and sulfolane mixture was 14 area percent.

Although no high molecular weight polysiloxanes were formed in either case, more cyclic and linear low molecular weight polysiloxanes were formed in the presence of sulfolane.

EXAMPLE 2

This example demonstrates the use of manganese oxide in the process of this invention. The procedure used was the same as Example 1 except that 22.0 g of MnO was used with 100 g of the masterbatch solution. The GLC results are presented in the following Table.

TABLE II

| | REACTANTS | |
|---|---|---|
| PRODUCTS | MnO | MnO + sulfolane |
| Cyclics: | | |
| D3 (%): | 0.05 | 1.46 |
| D4 (%): | 0.04 | 0.75 |
| D5 (%): | 0.03 | 0.20 |
| D6 (%): | 0 | 0.07 |
| TOTAL (%): | 0.12 | 2.56 |
| Linears: | | |
| ClDCl (%): | 0 | 0.51 |
| ClD2Cl (%): | 0 | 1.07 |
| ClD3Cl (%): | 0 | 0.64 |
| ClD4Cl (%): | 0 | 0.25 |
| TOTAL (%): | 0 | 2.47 |

The amount of dimethyldichlorosilane consumed in the reaction with the metal oxide alone was less than 2 area percent. The amount of dimethyldichlorosilane consumed in the reaction in the presence of the metal oxide and sulfolane mixture was 37 area percent.

Although no high molecular weight polysiloxanes were formed in either case, more cyclic and linear low molecular weight polysiloxanes were formed in the presence of sulfolane. In fact linear polysiloxanes were found only when sulfolane was present.

EXAMPLE 3

This example demonstrates the use of copper (II) oxide in the process of this invention. The procedure used was the same as Example 1 except that 24.8 g of CuO was used with 100 g of the masterbatch solution. The GLC results are presented in the following Table.

TABLE III

| | REACTANTS | |
|---|---|---|
| PRODUCTS | CuO | CuO + sulfolane |
| Cyclics: | | |
| D3 (%): | 0.06 | 0.09 |
| D4 (%): | 0.39 | 0.49 |
| D5 (%): | 0.18 | 0.20 |
| D6 (%): | 0.08 | 0.08 |
| TOTAL (%): | 0.71 | 0.86 |
| Linears: | | |
| ClDCl (%): | 1.02 | 0.92 |
| ClD2Cl (%): | 0.98 | 1.39 |
| ClD3Cl (%): | 0.51 | 0.87 |
| ClD4Cl (%): | 0.19 | 0.40 |
| TOTAL (%): | 2.70 | 3.58 |

The amount of dimethyldichlorosilane consumed in the reaction with the metal oxide alone was 10 area percent. The amount of dimethyldichlorosilane consumed in the reaction in the presence of the metal oxide and sulfolane mixture was 12 area percent.

Although no high molecular weight polysiloxanes were formed in either case, more cyclic and linear low molecular weight polysiloxanes were formed in the presence of sulfolane.

EXAMPLE 4

This example demonstrates the use of iron oxide in the process of this invention. The procedure used was the same as Example 1 except that 16.5 g of $Fe_2O_3$ was used with 100 g of the masterbatch solution. The GLC results are presented in the following Table.

TABLE IV

| | REACTANTS | |
|---|---|---|
| PRODUCTS | $Fe_2O_3$ | $Fe_2O_3$ + sulfolane |
| Cyclics: | | |
| D3 (%): | 0.11 | 0.10 |
| D4 (%): | 2.22 | 4.30 |
| D5 (%): | 0.85 | 2.13 |
| D6 (%): | 0.21 | 0.37 |
| TOTAL (%): | 3.39 | 6.96 |
| Linears: | | |
| ClDCl (%): | 0.23 | 0 |
| ClD2Cl (%): | 0.34 | 0 |
| ClD3Cl (%): | 0.26 | 0 |
| ClD4Cl (%): | 0.12 | 0 |
| TOTAL (%): | 0.95 | 0 |

The amount of dimethyldichlorosilane consumed in the reaction with the metal oxide alone was 49 area percent. The amount of dimethyldichlorosilane consumed in the reaction in the presence of the metal oxide and sulfolane mixture was greater than 95 area percent.

More cyclic low molecular weight polysiloxanes were produced in the presence of sulfolane. When only $Fe_2O_3$ was present no high molecular weight polysiloxane was produced. Upon the addition of sulfolane a high molecular weight polysiloxane (molecular weight of 1365 g/mole by GPC) was obtained.

EXAMPLE 5

This example demonstrates the use of magnesium oxide in the process of this invention. The procedure used was the same as Example 1 except that 12.4 g of MgO was used with 100 g of the masterbatch solution. The GLC results are presented in the following Table.

TABLE V

| PRODUCTS | REACTANTS | |
|---|---|---|
| | MgO | MgO + sulfolane |
| Cyclics: | | |
| D3 (%): | 0.10 | 3.30 |
| D4 (%): | 0.20 | 2.32 |
| D5 (%): | 0.12 | 0.67 |
| D6 (%): | 0.06 | 0.15 |
| TOTAL (%): | 0.48 | 6.44 |

The amount of dimethyldichlorosilane consumed in the reaction with the metal oxide alone was less than 2 area percent. The amount of dimethyldichlorosilane consumed in the reaction in the presence of the metal oxide and sulfolane mixture was 93 area percent.

No linear low molecular weight polysiloxanes were found in either case using MgO. More cyclic low molecular weight polysiloxanes were produced in the presence of sulfolane. When only MgO was present no high molecular weight polysiloxane was produced. Upon the addition of sulfolane a high molecular weight polysiloxane (molecular weight of 2290 g/mole by GPC) was obtained.

EXAMPLE 6

This example demonstrates the use of calcium oxide in the process of this invention. The procedure used was the same as Example 1 except that 17.4 g of CaO was used with 100 g of the masterbatch solution. The GLC results are presented in the following Table.

TABLE VI

| PRODUCTS | REACTANTS | |
|---|---|---|
| | CaO | CaO + sulfolane |
| Cyclics: | | |
| D3 (%): | 0.13 | 2.08 |
| D4 (%): | 0.42 | 3.26 |
| D5 (%): | 0.14 | 0.84 |
| D6 (%): | 0.07 | 0.24 |
| TOTAL (%): | 0.76 | 6.42 |

The amount of dimethyldichlorosilane consumed in the reaction with the metal oxide alone was 11 area percent. The amount of dimethyldichlorosilane consumed in the reaction in the presence of the metal oxide and sulfolane mixture was 93 area percent.

No linear low molecular weight polysiloxanes were found in either case using CaO. More cyclic low molecular weight polysiloxanes were produced in the presence of sulfolane. When only CaO was present no high molecular weight polysiloxane was produced. Upon the addition of sulfolane a high molecular weight polysiloxane (molecular weight of 3350 g/mole by GPC) was obtained.

EXAMPLE 7

This example demonstrates the use of mercury oxide in the process of this invention. The procedure used was the same as Example 1 except that 66.7 g of HgO was used with 100 g of the masterbatch solution. The GLC results are presented in the following Table.

TABLE VII

| PRODUCTS | REACTANTS | |
|---|---|---|
| | HgO | HgO + sulfolane |
| Cyclics: | | |
| D3 (%): | 0.62 | 2.15 |
| D4 (%): | 0.68 | 1.88 |
| D5 (%): | 0.42 | 0.90 |
| D6 (%): | 0.27 | 0.49 |
| TOTAL (%): | 1.99 | 5.42 |
| Linears: | | |
| ClDCl (%): | 0.22 | 0 |
| ClD2Cl (%): | 0.46 | 0 |
| ClD3Cl (%): | 0.29 | 0 |
| ClD4Cl (%): | 0.11 | 0 |
| TOTAL (%): | 1.08 | 0 |

The amount of dimethyldichlorosilane consumed in the reaction with the metal oxide alone was 29 area percent. The amount of dimethyldichlorosilane consumed in the reaction in the presence of the metal oxide and sulfolane mixture was 78 area percent.

More cyclic low molecular weight polysiloxanes were produced in the presence of sulfolane. When only HgO was present no high molecular weight polysiloxane was produced. Upon the addition of sulfolane a high molecular weight polysiloxane (molecular weight of 7680 g/mole by GPC) was obtained.

EXAMPLE 8

This example demonstrates the use of cadmium oxide in the process of this invention. The procedure used was the same as Example 1 except that b 39.7 g of CdO was used with 100 g of the masterbatch solution. The GLC results are presented in the following Table.

TABLE VIII

| PRODUCTS | REACTANTS | |
|---|---|---|
| | CdO | CdO + sulfolane |
| Cyclics: | | |
| D3 (%): | 0.03 | 4.44 |
| D4 (%): | 0.05 | 1.73 |
| D5 (%): | 0.04 | 0.44 |
| D6 (%): | 0 | 0.14 |
| TOTAL (%): | 0.12 | 6.75 |
| Linears: | | |
| ClDCl (%): | 0.82 | 0 |
| ClD2Cl (%): | 0.22 | 0 |
| ClD3Cl (%): | 0 | 0 |
| ClD4Cl (%): | 0 | 0 |
| TOTAL (%): | 1.04 | 0 |

The amount of dimethyldichlorosilane consumed in the reaction with the metal oxide alone was less than 2 area percent. The amount of dimethyldichlorosilane consumed in the reaction in the presence of the metal oxide and sulfolane mixture was 97 area percent.

More cyclic low molecular weight polysiloxanes were produced in the presence of sulfolane. When only CdO was present no high molecular weight polysiloxane was produced. Upon the addition of sulfolane a high molecular weight polysiloxane (molecular weight of 940 g/mole by GPC) was obtained.

EXAMPLE 9

This example demonstrates the use of tin oxide in the process of this invention. The procedure used was the same as Example 1 except that 41.9 g of SnO was used with 100 g of the masterbatch solution. The GLC results are presented in the following Table.

TABLE VIX

| PRODUCTS | REACTANTS | |
|---|---|---|
| | SnO | SnO + sulfolane |
| Cyclics: | | |
| D3 (%): | 0.05 | 2.87 |
| D4 (%): | 0.34 | 2.35 |
| D5 (%): | 0.17 | 0.84 |
| D6 (%): | 0.05 | 0.37 |
| TOTAL (%): | 0.61 | 6.43 |
| Linears: | | |
| ClDCl (%): | 0.14 | 0 |
| ClD2Cl (%): | 0.11 | 0 |
| ClD3Cl (%): | 0.07 | 0 |
| ClD4Cl (%): | 0.03 | 0 |
| TOTAL (%): | 0.35 | 0 |

The amount of dimethyldichlorosilane consumed in the reaction with the metal oxide alone or the metal oxide and sulfolane mixture was less than 2 area percent.

More cyclic low molecular weight polysiloxanes were produced in the presence of sulfolane. When only SnO was present no high molecular weight polysiloxane was produced. Upon the addition of sulfolane a high molecular weight polysiloxane (molecular weight of 1300 g/mole by GPC) was obtained.

EXAMPLE 10

This example demonstrates the use of several other metallic oxides in the process of this invention. The procedure used was the same as Example 1 except for the different metallic oxides used. The metallic oxides used were zinc oxide, antimony (III) oxide, antimony (V) oxide, thalium (III) oxide, and indium oxide. In all cases about equal amounts of low molecular weight polysiloxanes were obtained both in the absence and presence of sulfolane. No linear low molecular weight were observed either in the absence or presence of sulfolane. High molecular weight polymers were observed in both the absence and presence of sulfolane. The results are presented in the Table below.

TABLE X

| Metal Oxide | | No Sulfolane | | Added Sulfolane | |
|---|---|---|---|---|---|
| ID | Wt (g)* | Total Cyclics (area %) | Polymer Peak MW (g/mol) | Total Cyclics (area %) | Polymer Peak MW (g/mol) |
| ZnO | 25.1 | 5.01 | 11,000 | 5.16 | 12,000 |
| Sb2O3 | 30.2 | 4.63 | — | 5.59 | 1560 |
| Sb2O5 | 18.8 | 1.22 | — | 1.71 | 2050 |
| Tl2O3 | 47.1 | 2.36 | — | 2.45 | 1160 |
| In2O3 | 28.7 | 9.84 | — | 9.39 | 10,000 |

*The weight of metal oxide added per 100 g of masterbatch solution.

The amount of dimethyldichlorosilane consumed in the reaction with ZnO alone was 97 area percent. The amount of dimethyldichlorosilane consumed in the reaction in the presence of the ZnO and sulfolane mixture was greater than 99 area percent.

The amount of dimethyldichlorosilane consumed in the reaction with Sb2O3 alone was 67 area percent. The amount of dimethyldichlorosilane consumed in the reaction in the presence of the Sb2O3 and sulfolane mixture was 81 area percent.

EXAMPLE 11

This example employs antimony (III) oxide as the metal oxide and shows polymerization in the presence and absence of sulfolane. Sb2O3 (30.2 g) was added to two separate samples of the masterbatch solution (100 g in each case). Sulfolane (223 g) was added to one of the Sb2O3 containing mixtures. Both solutions were stirred at room temperature and analyzed by GLC after 5, 30 and 60 minutes. The results are shown below.

TABLE XI

| | No Sulfolane Time (min) | | | Added Sulfolane Time (min) | | |
|---|---|---|---|---|---|---|
| | 5 | 30 | 60 | 5 | 30 | 60 |
| D3 | 0.07 | 0.06 | 0.03 | 2.47 | 2.73 | 2.87 |
| D4 | 1.71 | 2.13 | 2.19 | 2.22 | 2.40 | 2.58 |
| D5 | 1.80 | 2.27 | 2.28 | 0.81 | 0.87 | 0.94 |
| D6 | 0.85 | 0.32 | 1.07 | 0.30 | 0.33 | 0.35 |
| Total | 4.43 | 4.78 | 5.57 | 5.80 | 6.33 | 6.74 |

The sulfolane containing sample produced higher levels of cyclics and produced the cyclics at a faster rate. This demonstrates that sulfolane promotes the siloxane forming reaction in the presence of a metal oxide.

EXAMPLE 12

A mixture of Fe2O3 (25.2 g) and dimethyldichlorosilane (55.7 g) were refluxed together for five hours. GLC analysis indicated 63 area percent unreacted (CH3)2SiCl2 and 25 area percent (CH3)2ClSiOSi(CH3)2Cl with the remainder being higher molecular weight oligomers and cyclics. The reaction mixture was cooled and sulfolane (114 g) was added. Upon heating to 40° C. a mild exotherm was observed and a polydimethylsiloxane fluid floated to the surface. The siloxane fluid had a bulk viscosity of 20 cs measured with a Cannon-Fenske viscometer. Based on the viscosity, the siloxane fluid had a molecular weight of about 1900-2000 g/mole. GLC indicated almost complete consumption of the dimethyldichlorosilane. A solid residue was recovered from the reaction mixture. The solid residue contained unreacted iron (III) oxide and an iron chloride sulfolane complex.

COMPARATIVE EXAMPLE 1

Dimethyldiclorosilane (60 g) and sulfolane (115 g) were heated together. No metal oxides were added. The sulfolane contained less than 400 ppm water. No siloxane fluids were obtained. This Comparative Example demonstrates that the polysiloxane formation observed in this invention did not result from either the traces of water present in the sulfolane or by reaction of the chlorosilane with the sulfolane alone.

COMPARATIVE EXAMPLE 2

This example shows several metal oxide, sulfolane, and halosilane combination which do not give significantly improved polysiloxane formation. The procedure used was the same as Example 1 except that 23.4 g of SnO2, 10.5 g of Al2O3, or 17.2 g of Co2O3 were used with 100 g of the masterbatch solution. The GLC results are presented for SnO2 in the following Table.

TABLE VII

| PRODUCTS | REACTANTS | |
|---|---|---|
| | SnO2 | SnO2 + sulfolane |
| Cyclics: | | |
| D3 (%): | 0 | 0.02 |
| D4 (%): | 0.04 | 0.05 |
| D5 (%): | 0 | 0.02 |
| D6 (%): | 0 | 0 |

TABLE VII-continued

| PRODUCTS | REACTANTS | |
|---|---|---|
| | SnO$_2$ | SnO$_2$ + sulfolane |
| TOTAL (%): | 0.04 | 0.09 |
| Linears: | | |
| ClDCl (%): | 0 | 0.09 |
| ClD2Cl (%): | 0.03 | 0.02 |
| ClD3Cl (%): | 0 | 0 |
| ClD4Cl (%): | 0 | 0 |
| TOTAL (%): | 0.03 | 0.11 |

The GLC results are presented for Al$_2$O$_3$ in the following Table.

TABLE XIII

| PRODUCTS | REACTANTS | |
|---|---|---|
| | Al$_2$O$_3$ | Al$_2$O$_3$ + sulfolane |
| Cyclics: | | |
| D3 (%): | 0.10 | 0.08 |
| D4 (%): | 0.11 | 0.06 |
| D5 (%): | 0.05 | 0.02 |
| D6 (%): | 0.02 | 0 |
| TOTAL (%): | 0.28 | 0.16 |
| Linears: | | |
| ClDCl (%): | 2.30 | 2.35 |
| ClD2Cl (%): | 0.34 | 0.53 |
| ClD3Cl (%): | 0.08 | 0 |
| ClD4Cl (%): | 0 | 0 |
| TOTAL (%): | 2.72 | 2.88 |

The GLC results are presented for Co$_2$O$_3$ in the following Table.

TABLE XIV

| PRODUCTS | REACTANTS | |
|---|---|---|
| | Co$_2$O$_3$ | Co$_2$O$_3$ + sulfolane |
| Cyclics: | | |
| D3 (%): | 0.02 | 0.11 |
| D4 (%): | 0.07 | 0.11 |
| D5 (%): | 0.03 | 0.04 |
| D6 (%): | 0 | 0.02 |
| TOTAL (%): | 0.12 | 0.28 |
| Linears: | | |
| ClDCl (%): | 0.07 | 0.23 |
| ClD2Cl (%): | 0.04 | 0.07 |
| ClD3Cl (%): | 0 | 0.03 |
| ClD4Cl (%): | 0 | 0 |
| TOTAL (%): | 0.11 | 0.33 |

No high molecular weight polysiloxanes were observed with SnO$_2$, Al$_2$O$_3$, or Co$_2$O$_3$ in the presence or absence of sulfolane.

That which is claimed is:

1. A method for producing polysiloxanes, said method comprising (1) reacting a halosilane or mixture of halosilanes in the presence of a metal oxide or mixture of metal oxides and sulfolane wherein polysiloxanes are formed from said halosilane or mixture of halosilanes and wherein said metal oxide or mixture of metal oxides forms a metal halogen complex or mixed metal halogen complex with said sulfolane and (2) thereafter separating the polysiloxanes.

2. A method as defined in claim 1 wherein said halosilane or mixture of halosilanes, said metal oxide or mixture of metal oxides and sulfolane are reacted under essentially anhydrous conditions.

3. A method as defined in claim 1 wherein said halosilane or mixture of halosilanes are described by the general formula $$R_ySiX_{(4-y)}$$

where R is an organic radical attached to silicon through a Si—C bond, or an organic radical attached to silicon through a Si—O bond, or hydrogen; where X is a halogen; and where y is 1 or 2.

4. A method as defined in claim 2 wherein said halosilane or mixture of halosilanes are described by the general formula $$R_ySiX_{(4-y)}$$

where R is an organic radical attached to silicon through a Si—C bond, or an organic radical attached to silicon through a Si—O bond, or hydrogen; where X is a halogen; and where y is 1 or 2.

5. A method as defined in claim 3 wherein X is chlorine or bromine.

6. A method as defined in claim 4 wherein X is chlorine or bromine.

7. A method as defined in claim 5 wherein said metal oxide or mixture of metal oxides are selected from the group consisting of antimony (III) oxide, antimony (V) oxide, cadmium oxide, calcium oxide, copper (II) oxide, indium oxide, iron (II) oxide, iron (III) oxide, magnesium oxide, manganese (II) oxide, mercury (II) oxide, nickel (II) oxide, thallium (III) oxide, tin (II) oxide, and zinc oxide.

8. A method as defined in claim 6 wherein said metal oxide or mixture of metal oxides are selected from the group consisting of antimony (III) oxide, antimony (V) oxide, cadmium oxide, calcium oxide, copper (II) oxide, indium oxide, iron (II) oxide, iron (III) oxide, magnesium oxide, manganese (II) oxide, mercury (II) oxide, nickel (II) oxide, thallium (III) oxide, tin (II) oxide, and zinc oxide.

9. A method as defined in claim 7 wherein said metal oxide or mixture of metal oxides are selected from the group consisting of cadmium oxide, calcium oxide, iron (II) oxide, iron (III) oxide, magnesium oxide, mercury (II) oxide, and tin (II) oxide.

10. A method as defined in claim 8 wherein said metal oxide or mixture of metal oxides are selected from the group consisting of cadmium oxide, calcium oxide, iron (II) oxide, iron (III) oxide, magnesium oxide, mercury (II) oxide, and tin (II) oxide.

11. A method as defined in claim 9 wherein said metal oxide is iron (III) oxide.

12. A method as defined in claim 10 wherein said metal oxide is iron (III) oxide.

13. A method as defined in claim 10 wherein said X in said halosilane or mixture of halosilanes is chlorine and wherein the reaction temperature is between room temperature and 100° C.

14. A method as defined in claim 11 wherein said X in said halosilane or mixture of halosilanes is chlorine and wherein the reaction temperature is between room temperature and 100° C.

15. A method as defined in claim 12 wherein said X in said halosilane or mixture of halosilanes is chlorine and wherein the reaction temperature is between room temperature and 100° C.

16. A method as defined in claim 13 wherein said X in said halosilane or mixture of halosilanes is chlorine and wherein the reaction temperature is between room temperature and 100° C.

17. A method for producing polysiloxanes, said method comprising (1) reacting a halosilane or mixture of halosilanes in the presence of a metal oxide or mixture of metal oxides and sulfolane wherein said metal oxide or mixture of metal oxides are selected from the group consisting of antimony (III) oxide, antimony (V) oxide, cadmium oxide, calcium oxide, copper (II) oxide, indium oxide, iron (II) oxide, iron (III) oxide, magnesium oxide, manganese (II) oxide, mercury (II) oxide, nickel (II) oxide, thallium (III) oxide, tin (II) oxide, and zinc oxide and thereafter (2) separating the polysiloxanes.

18. A method as defined in claim 17 wherein said halosilane or mixture of halosilanes, said metal oxide or mixture of metal oxides and sulfolane are reacted under essentially anhydrous conditions.

19. A method as defined in claim 17 wherein said halosilane or mixture of halosilanes are described by the general formula

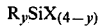

$$R_y SiX_{(4-y)}$$

where R is an organic radical attached to silicon through a Si—C bond, or an organic radical attached to silicon through a Si—O bond, or hydrogen; where X is a halogen; and where y is 1 or 2.

20. A method as defined in claim 18 wherein said halosilane or mixture of halosilanes are described by the general formula

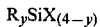

$$R_y SiX_{(4-y)}$$

where R is an organic radical attached to silicon through a Si—C bond, or an organic radical attached to silicon through a Si—O bond, or hydrogen; where X is a halogen; and where y is 1 or 2.

21. A method as defined in claim 19 wherein X is chlorine or bromine.

22. A method as defined in claim 20 wherein X is chlorine or bromine.

23. A method as defined in claim 21 wherein said metal oxide or mixture of metal oxides are selected from the group consisting of cadmium oxide, calcium oxide, iron (II) oxide, iron (III) oxide, magnesium oxide, mercury (II) oxide, and tin (II) oxide.

24. A method as defined in claim 22 wherein said metal oxide or mixture of metal oxides are selected from the group consisting of cadmium oxide, calcium oxide, iron (II) oxide, iron (III) oxide, magnesium oxide, mercury (II) oxide, and tin (II) oxide.

25. A method as defined in claim 23 wherein said metal oxide is iron (III) oxide.

26. A method as defined in claim 24 wherein said metal oxide is iron (III) oxide.

27. A method as defined in claim 23 wherein said X in said halosilane or mixture of halosilanes is chlorine and wherein the reaction temperature is between room temperature and 100° C.

28. A method as defined in claim 24 wherein said X in said halosilane or mixture of halosilanes is chlorine and wherein the reaction temperature is between room temperature and 100° C.

29. A method as defined in claim 25 wherein said X in said halosilane or mixture of halosilanes is chlorine and wherein the reaction temperature is between room temperature and 100° C.

30. A method as defined in claim 26 wherein said X in said halosilane or mixture of halosilanes is chlorine and wherein the reaction temperature is between room temperature and 100° C.

* * * * *